United States Patent
Blake et al.

(10) Patent No.: US 7,332,173 B2
(45) Date of Patent: Feb. 19, 2008

(54) GROUP A STREPTOCOCCAL POLYSACCHARIDE IMMUNOGENIC COMPOSITIONS AND METHODS

(75) Inventors: Milan S. Blake, New York, NY (US); John B. Zabriskie, New York, NY (US); Joseph Y. Tai, Fort Washington, PA (US); Francis Michon, Laurel, MD (US)

(73) Assignees: The Rockefeller University, New York, NY (US); Baxter International Inc., Deerfield, IL (US)

( * ) Notice: Subject to any disclaimer, the term of this patent is extended or adjusted under 35 U.S.C. 154(b) by 0 days.

(21) Appl. No.: 11/086,214

(22) Filed: Mar. 21, 2005

(65) Prior Publication Data

US 2005/0163808 A1    Jul. 28, 2005

Related U.S. Application Data

(63) Continuation of application No. 09/207,188, filed on Dec. 8, 1998, now abandoned, which is a continuation of application No. 08/231,229, filed on Apr. 21, 1994, now Pat. No. 5,866,135.

(51) Int. Cl.
*A61K 39/02* (2006.01)
*A61K 39/00* (2006.01)
*A61K 38/00* (2006.01)
*C07H 1/00* (2006.01)

(52) U.S. Cl. .............................. 424/244.1; 424/234.1; 424/184.1; 424/831; 514/23; 536/123.1

(58) Field of Classification Search ............. 424/244.1, 424/234.1, 184.1, 831; 536/123.1; 514/23
See application file for complete search history.

(56) References Cited

U.S. PATENT DOCUMENTS 5,866,135 A * 2/1999 Blake et al. ............ 424/197.11

FOREIGN PATENT DOCUMENTS

| EP | 186 576 | 7/1986 |
|---|---|---|
| WO | WO 93/07178 | 4/1993 |
| WO | WO 94/06467 | 3/1994 |

OTHER PUBLICATIONS

Shackelford et al. J. Immunol. 140: 3200-3205, 1988.*
Salvadori et al. J. Infect. Dis. 171: 593-600, 1995.*
Knigge et al. J. Clin. Microbiol. 20: 735-741, 1984.*
Gupta et al. Indian J. Med. Res. A 97: 25-31, 1993.*
Michon et al. Canadian J. Infect. Dis. 6: Suppl. C, Jul. 1995.*
Laffariere et al. Vaccine 15: 179-186, 1997.*
Fischetti et al. J. Immunol. 130: 896-902, 1983.*
Sabharwal et al. In: Proceedings of the XIV Lancefiled International Symposium on Streptococci and Streptococcal Diseases, Auckland, New Zealand, Oct. 11-15, 1999.*
Szu et al. Infect. Immun. 54: 448-455, 1986.*
Nielsen et al. Microbial Pathogenesis 14: 299-305, 1993, abstract.*
Peeters et al. Med. Microbiol. Immunol. 181: 35-42, 1992.*
K.B. Reimer, et al., "Immunochemical Characterization of Polyclonal and Monoclonal Streptococus Group A Antibodies by Chemically Defined Glycoconjugates and Synthetic Oligosaccharides", *Carbohydrate Research*, 232:131-142 (1992).
H.M. Fillit, et al., "Immunogenicity of Liposome-Bound Hyaluronate in Mice", *J. Exp. Med.* 168:971-982 (1988).
H.M. Fillit, et al., "Induction of Antibodies to Hyaluronic Acid by Immunication of Rabbits With Encapsulated Streptococci", *J. Exp. Med.* 164:762-776 (1986).
J. Rotta, et al., "Biological Properties of Cell Wall Mucopeptide of Hemolytic Streptococci", Institute of Epidemiology and Microbiology, Prague, Czech; First Institute of Pathology, Charles University, Prague, Czech; pp. 31-47 (1969).
Pinto et al. (1991) *Carbohydrate Res.* 210:199-219.
Pinto et al. (1983) *Carbohydrate Res.* 124:313-318.
Andrews et al. (1990) *J. Chem. Soc. Perkin Trans.* 1(6) 1785-92.
Reimer et al. (1992) *Carbohydrate Res.* 228(2):399-414.
Reimer et al. (1988) *J. Chem. Soc. Perkin Trans.* 1(8):2103-11.
McCarthy M. (1956) *J. Exp. Med.* 104:629-643.
Dick, Jr. et al. (1989) Conjugate Vacines, Contrib. Microbiol. Immunol. 10:48-114.
Bruyere et al. (1987) *Vaccine* 5:39-42.
R.A. Zimmerman, et al., "Precipitating Antibody to Group A Streptococcal Polysaccharide in Humans", *J. of Immuno.*, No. 3, 107:832-841 (1971).
W.W. Karakawa, et al., "Detection of Streptococcal Group-Specific Antibodies in Human Sera", *J. of Experimental Medicine*, No. 2, 122:195-205, (1965).
R.C. Lancefield, "Presistence of Type-Specific Antibodies in Man Following Infection With Group A Streptococci", *J. of Experimental Medicine*, 110:271-292 (1959).
W.C. Schmidt, et al., "The Determination of Antibody to a Group A Streptococcal Polysaccharide in Human Sera by Hemaggluntination"" *Journal of Exp. Med.*, No. 4, 121:793-806 (1965).

* cited by examiner

*Primary Examiner*—S. Devi
(74) *Attorney, Agent, or Firm*—Morgan & Finnegan, LLP

(57) ABSTRACT

This invention provides a novel immunogenic composition and vaccine, processes for producing them and methods for immunization against infections and disease caused by group A Streptococci. The compositions include group A streptococcal polysaccharide covalently linked to protein or liposomes to form immunogenic conjugates. The method of immunization for this invention comprises administering to an individual an immunogenic amount of group A polysaccharide. The group A polysaccharide may be administered as a vaccine either on its own, conjugated to proteins or conjugated to liposomes. Additionally, the group A polysaccharides may be associated with an adjuvant. This invention is particularly useful for providing both active and passive immunogenic protection for those populations most at risk of contracting group A Streptococcal infections and disease namely adults, pregnant women and in particular infants and children.

20 Claims, 9 Drawing Sheets

FIG. 1
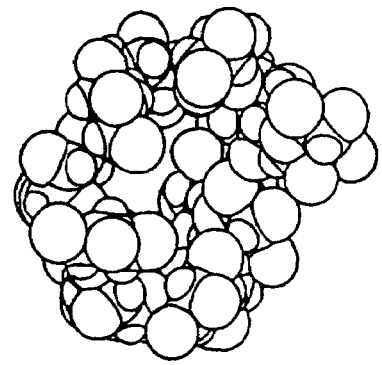
A  Group A Carbohydrate
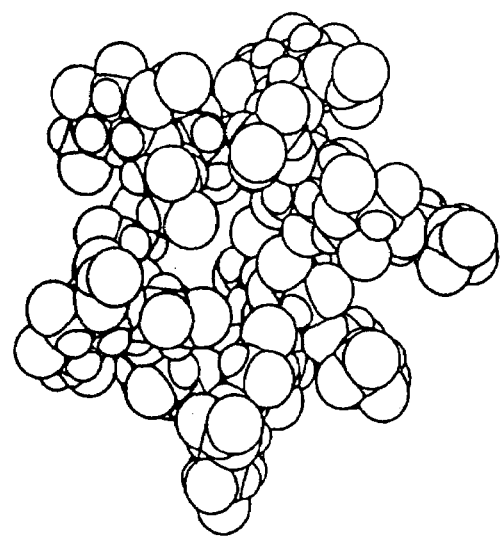
B  Group A variant Carbohydrate
[Rha(α1.3)Rha(α1.2)Rha(α1.3)Rha(α1.2)Rha]
        |β1.3                    |β1.3
        GlcNac                   GlcNac
[Rha(α1.3)Rha(α1.2)Rha(α1.3)Rha(α1.2)Rha]

FIG. 4
A
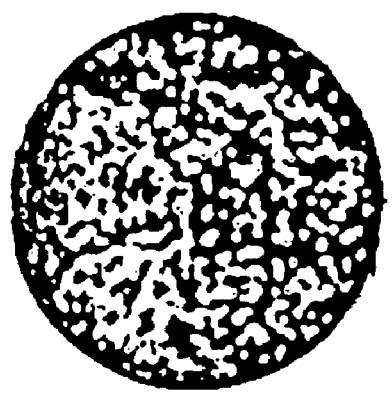
B
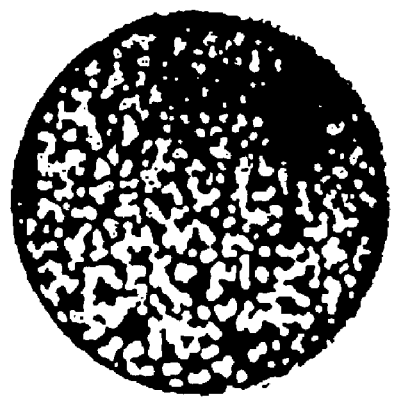
C
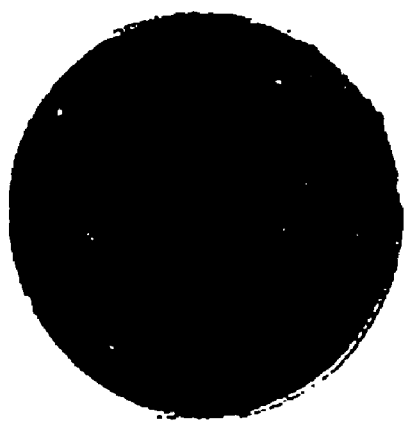

GROUP A STREPTOCOCCAL POLYSACCHARIDE IMMUNOGENIC COMPOSITIONS AND METHODS

This application is a continuation of U.S. patent application Ser. No. 09/207,188, filed Dec. 8, 1998, now abandoned, which is a continuation of application Ser. No. 08/231,229, filed Apr. 21, 1994, now U.S. Pat. No. 5,866,135.

FIELD OF THE INVENTION

This invention relates to the field of novel immunogenic compositions, processes for producing them and methods for immunization of warm-blooded animals, including humans, against infections and disease caused by group A Streptococci.

BACKGROUND OF THE INVENTION

Group A Streptococcal disease as shown by the rate of infections by age group is a childhood disease (1-3). Much like the other diseases in this category such as meningococcal (4) and *Haemophilus meningitis* (5), diphtheria (6) and others (7,8), the majority of cases occur in young children and the rate of infection decreases with age. Thus, by the age of eighteen years, the incidence of group A Streptococcal infections is relatively low (1-3). This would suggest that some type of natural immunity to this group of organisms may occur over time much like that found with other childhood infections.

In experiments extending over several decades, Lancefield and colleagues (9-11) established that the vast majority of hemolytic streptococci infecting humans were group A. This distinction was based on serological reactions to group A Streptococcal carbohydrate. Later studies reported that the immunodominant determinant was N-acetylglucosamine (12,13). Using mouse protection tests and precipitin assays, these group A Streptococci were further sub-divided into serotypes based on the presence of antigenically different M proteins present on the surface of the organism. It has been clearly shown that antibodies directed against a specific M serotype are protective in a mouse model of infection (14). In humans, recovery from group A Streptococcal infection is often associated with long lasting immunity which is type specific to the infecting organism (11). But in both cases, the protection is M serotype-specific and does not extend to protection against other serotypes. In addition, it has been demonstrated in numerous studies that human sera rarely contain multiple M protein serotype specific antibodies (11,15). These classical experiments, both in humans and experimental animals, established an important role of the M protein in the virulence of group A Streptococci and have formed the basis for numerous unsuccessful attempts to develop streptococcal vaccines that would elicit protective antibodies either toward the amino-terminal portion of the M protein in which the serotypic specificity resides or more recently to the common C-repeat regions of the molecule (16).

However, in view of the age related nature of group A infections which suggests a rise in natural immunity to this group of bacteria, the question remains whether this represents a slow rise in antibodies directed at more common regions on the M protein or whether other surface antigens which have received less attention might play a role in this naturally acquired nonserotype specific protection. For example, the hyaluronic acid capsule plays an important role in the virulence of group C infections in guinea pigs (17) and anti-hyaluronate antibodies have been detected in animals (18, 34) and humans (19). Hyaluronic acid from group A Streptococci was reported as being immunogenic in rabbits after immunization with formalized, encapsulated group A Streptococci or bound to liposomes (18). Use of liposomes in vaccines has also been reported (31). Injection of the mucopeptide fractions of the streptococcal cell wall induces a short lived protection in experimental animals (20) but its role in humans remains unknown.

The group specific carbohydrate consists of a poly-rhamnose backbone to which, in the case of Group A, an N-acetylglucosamine is present at the non-reducing terminal position (FIG. 1a). Group A variant streptococci have been described and characterized (12,13). In these streptococci, the poly-rhamnose backbone is present but remains undecorated by N-acetylglucosamine (FIG. 1b). In early experiments, rabbits were injected with whole group A Streptococci lacking M protein and this was shown to elicit precipitating antibodies to the group A carbohydrate. However, these antibodies were not passively protective against an M protein positive group A Streptococcal challenge in passive mouse protection studies (14). Furthermore, several earlier attempts to demonstrate similar precipitating antibodies in humans were unsuccessful, suggesting that precipitating carbohydrate antibodies did not play a significant role in protection against streptococcal infections.

However, because most of the early methods to detect a rise in antibodies depended on the ability of these antibodies to become precipitable with the addition of antigen, many antibodies which none-the-less were reactive with a specific antigen but did not precipitate in such assays, were left undetected. Antibodies reactive to the hyaluronic acid capsule of group A Streptococci provide one good example. In studies focused on eliminating this problem, a series of reports beginning in 1965 (21,22) employed both direct and indirect agglutination techniques to detect antibodies. Direct agglutination detected precipitating antibodies while the indirect agglutination would measure both precipitating and non-precipitating antibodies. Of interest was the demonstration by Karakawa et al (22) that the direct agglutinating antibodies, i.e. the precipitating antibodies, in these human sera were directed primarily against group A variant carbohydrate, the poly-rhamnose backbone, while the indirect agglutination techniques directed at the non-precipitating antibodies detected a high titer of antibodies to the N-acetylglucosamine determinant.

Subsequent studies by Zimmerman et al (23), employing human sera from a variety of streptococcal infections, indicated that the incidence of these non-precipitating antibodies varied from a low of 30% in a population, which had been carefully followed and treated for streptococcal infections, to a high of 84% in a population recently infected with group A Streptococci. They also noted that antibody titers to the group A carbohydrate peaked at age 17 and that there was no difference in antibody titers to this carbohydrate in rheumatics with and without heart disease. These results differed from those reported by Dudding and Ayoub in which anti-group A carbohydrate antibodies were persistently elevated in rheumatic heart disease patients compared to those without valvular damage (24).

The question of whether or not these antibodies play a role in protection has been difficult to assess. The classic opsonophagocytosis assay of Lancefield used selected whole human blood (15,25,26) to which hyperimmune rabbit sera with known M protein serotype specific antibodies were added. The selection of the whole human blood was based on two facts; (1) it contained no M protein reactive antibodies and/or (2) would not promote phagocytosis of streptococci in the absence of the serotype specific rabbit antiserum. The question whether the normal human sera per se could enhance phagocytosis was never really addressed.

SUMMARY OF THE INVENTION

This invention provides an immunogenic composition for protecting mammals against infection by group A Streptococcal bacteria. The immunogenic composition comprises an immunogenic amount of group A *Streptococcus* polysaccharide (GASP) having the following structure:

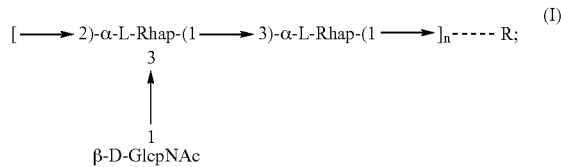

wherein R is a terminal reducing L-rhamnose or D-GlcpNAc and n is a number sufficiently large to define a polysaccharide of sufficient average molecular weight to provide an immunogenic response to the β-D-GlcpNAc residue glycosidically linked to position 3 of rhamnose and a carrier. This region of the GASP defines an epitope which induces the formation of bactericidal antibodies.

The GASP which is present in the immunogenic compositions may be in the form of free polysaccharide or as a component of a conjugate in which the GASP is covalently linked to phospholipid capable of forming a liposome or a protein. Native or recombinant bacterial protein such as tetanus toxoid, cholera toxin, diphtheria toxoid, or $CRM_{197}$ are examples of suitable proteins useful as conjugates. In another embodiment an immunogenic protein is incorporated into the liposome containing GASP covalently linked to phospholipid.

The immunogenic composition is also useful as a vaccine and may further comprise an adjuvant such as aluminum hydroxide, aluminum phosphate, monophosphoryl lipid A, QS21 or stearyl tyrosine. The immunogenic composition of this invention are capable of eliciting active and passive protection against infection by group A streptococcal infection. For passive protection, immunogenic antibodies are produced by immunizing a mammal with a vaccine made of the immunogenic composition of the invention and then recovering the immunogenic antibodies from the mammal.

This invention also provides methods of immunizing a mammal against infection by group A Streptococcal bacteria by administering an immunogenic amount of the compositions of the invention.

In another embodiment, this invention provides a method of making an immunogenic composition comprising covalently linking GASP to liposomes; dissolving the liposomes in a buffer suitable for solubilizing hydrophobic proteins; combining the dissolved liposomes with protein dissolved in buffer to form a complex of liposomes and protein. The protein/liposome complex is then separated from the buffer.

An object of this invention is to provide immunogenic compositions useful for raising antibodies which have application for prophylactic and diagnostic purposes. Another object of this invention is to provide a method for immunizing a mammal against group A Streptococcal bacteria by administering an immunogenic amount of GASP. Another object is to provide methods of covalently linking the GASP to a protein to form an immunogen conjugate. In a preferred embodiment, the conjugate has a formula of:

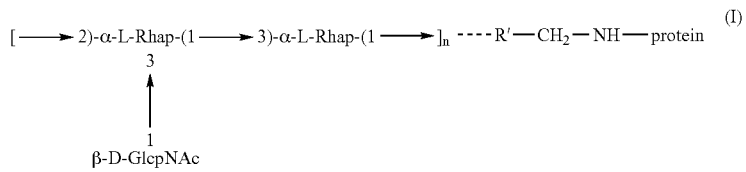

wherein R' is the product of reduction and oxidation of the terminal reducing sugar. A further object of this invention is the use of the immunogenic compositions to provide protection against infection by group A *Streptococcus* in those populations most at risk of contracting group A Streptococcal infections and disease namely adults, pregnant women and, in particular, infants and children.

BRIEF DESCRIPTION OF THE DRAWINGS

FIG. 1 schematically represents the structural design of group A carbohydrate (FIG. 1A) and the group A Variant carbohydrate (FIG. 1B). The depiction of the three dimensional structure of the group A carbohydrate clearly supports the observation that the serological specificity of the carbohydrate is directed towards the N-acetylglucosamine moiety of the carbohydrate.

FIG. 4 graphically illustrates the indirect bactericidal assay using washed human blood to which various sera were added to the tubes containing RPMI and complement as outlined in Example 1. The initial inoculum was nine CFU of group A-type 6 Streptococci. FIG. 4A shows the growth of the organism in the rotated tubes containing normal rabbit serum. FIG. 4B shows the growth in stationary tubes with human serum having a high ELISA titer reactive to the group A carbohydrate. FIG. 4C shows the inhibition of growth with the same human serum as in FIG. 4B but in a rotated tube.

DETAILED DESCRIPTION OF THE INVENTION

Figure 2:
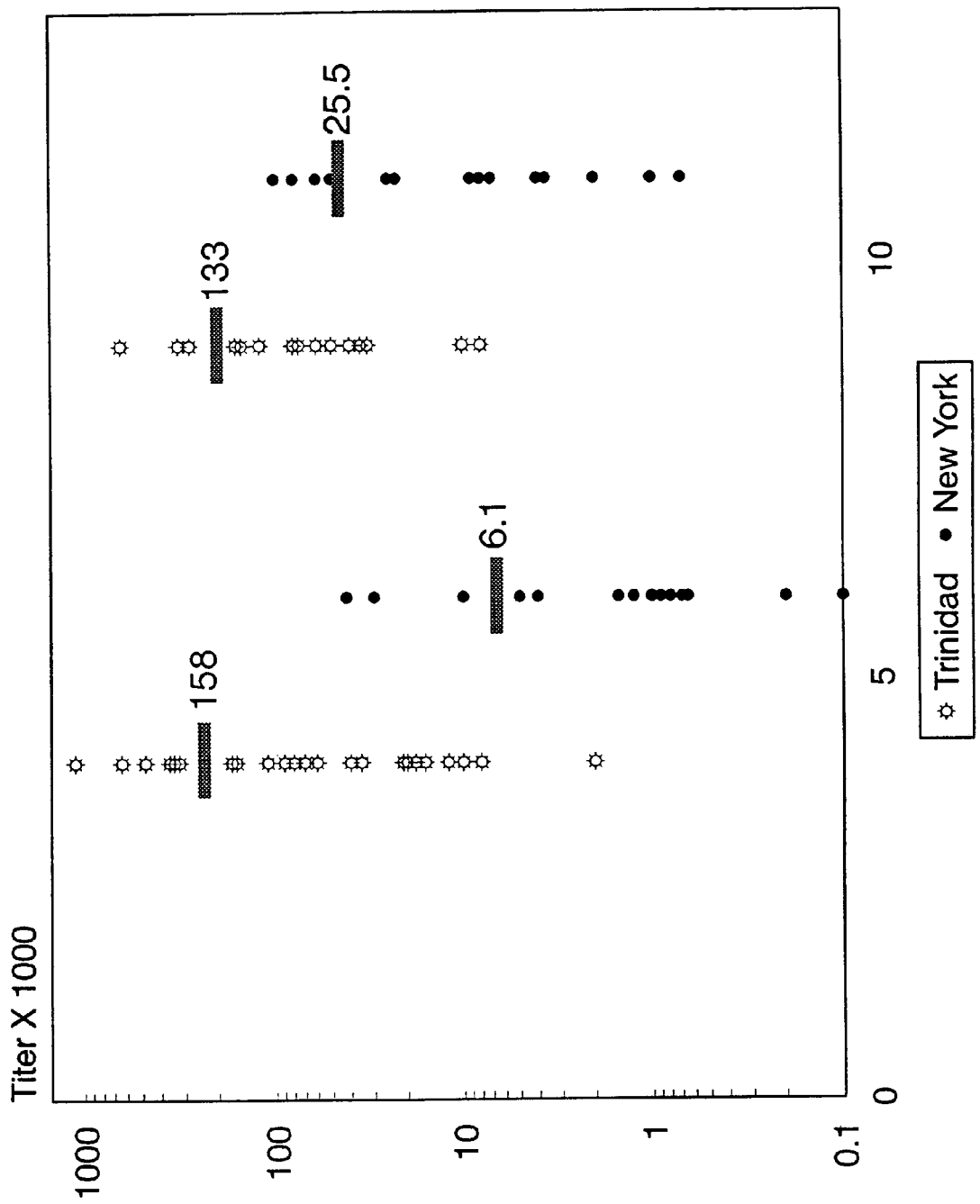
FIG. 2 graphically illustrates the ELISA titer determinations of group A Streptococcal carbohydrate antibodies in normal children at the age of 5 and 10 years old from Trinidad and New York. The readings were end point determinations of 1.0 OD at 405 nm.

In view of the known serological data detecting carbohydrate antibodies in human sera, coupled with the age related induction of protection by other carbohydrate antigens, namely, pneumococcal (27) meningococcal (4), and *Haemophilus* polysaccharides (5), we decided to reexamine various human sera for the presence of carbohydrate antibodies in both normal populations and in those with streptococcal infections. Also included in these studies were patients with post streptococcal sequelae. Purified group A carbohydrate was covalently linked to synthetic phosphatidylethanolamine, incorporated into liposomes, and used in an ELISA based assay. This invention demonstrates that antibodies to the group A carbohydrate antigen are readily detected in human sera. Furthermore, depending on the geographical population and exposure to streptococcal disease, the amount of these antibodies has an age related dependence. A rise in antibody titer to the group A carbohydrate was also demonstrated following a known streptococcal infection. To address the question whether or not these antibodies or a portion of these antibodies reactive to the group A carbohydrate could promote opsonophagocytosis, we used a modified Lancefield bactericidal assay. The resulting data demonstrate that these antibodies are opsonic and the epitope to which these opsonic group A carbohydrate antibodies are directed are the non-reducing terminal N-acetylglucosamine residues.

The invention provides both an immunogenic composition and method of immunization for protection in mammals, preferably humans, against infection by group A Streptococcal bacteria. The immunogenic conjugates of this invention are formed by covalently attaching group A *Streptococcus* polysaccharide (GASP) to a suitable protein or liposome forming phospholipid.

Isolation and growth of group A *Streptococcus* and preparation of the group A polysaccharide is accomplished according to the procedures as described by McCarty (28) and Dubois et al. (31) which are incorporated herein by reference. The isolated GASP has the following chemical structure:

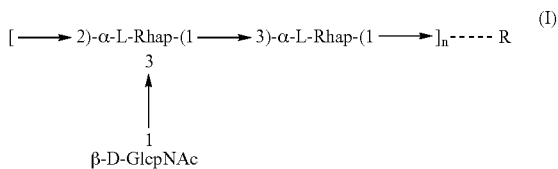

wherein R is a terminal reducing L-rhamnose or D-GlcpNAc and n is a number of repeat units sufficiently large to define a polysaccharide of sufficient average molecular weight to be immunogenic. Preferably n is from about 1 to about 50. Even more preferably, n is from about 3 to about 30 with an optimal amount of about 20. As used herein, the term polysaccharide is meant to include any polymer of saccharides and includes disaccharides, oligosaccharides, etc. Cultures of group A variant *Streptococcus*, which produce the above polysaccharide structure are deposited with the American Type Culture Collection, 10801 University Boulevard, Manassas, Va. 20110-2209. GASP should be of sufficient size to elicit an immunogenic response in individuals. Most preferably the average molecular weight is about 10 kilodaltons. A single repeat amount of the GASP has a molecular weight of about 500 daltons.

In a preferred embodiment of the invention, the GASP is covalently bound to protein to form a conjugate. Such conjugates preferably convert the immunogenic response to the polysaccharide for one which is T-cell independent to T-cell dependent. Accordingly, any protein or fragment thereof which is tolerated by the individual and capable of eliciting a T-cell dependent response is suitable for a conjugatory to GASP. Essentially any protein could serve as a conjugate protein. Specifically the selected protein must possess at least one free amino group for use in conjugation with the group A polysaccharide. Preferably, the protein is any native or recombinant bacterial protein and is itself an immunogen eliciting T-cell dependent responses in both young and adult mammals. Examples of such proteins include, but are not limited to, tetanus toxoid, cholera toxin, diphtheria toxoid and $CRM_{197}$. Other candidates for conjugate proteins include toxins or toxoids of pseudomonas, staphylococcus, streptococcus, pertussis and entertoxigenic bacteria including *Escherichia coli.*

In a preferred embodiment, the conjugate molecules of this invention comprise a protein core to which the GASP are bound through a modified form of the terminal reducing sugar. Such conjugate molecules would therefore comprise monofunctionalized GASP bound protein. Preferably a plurality of GASP, more specifically between about 1 and 12 GASP are bound to each protein. Most preferably, at least about 5 GASP are bound to each protein.

In another embodiment GASP are bound to protein through two or more sites on each GASP. Since the bactericidal epitope appears to be present on the branches of the GASP repeat units, functionalization of the GASP and linkage to protein should be effected in a manner which preserves an immunogenic amount of bactericidal epitope.

The proteins to which the GASP is conjugated may be native toxin or a detoxified toxin (i.e. toxoid). Also, nontoxic mutational forms of protein toxins may also be used. Preferably, such mutations retain epitopes of the native toxin. Such mutated toxins have been termed “cross reacting materials”, or CRMs. $CRM_{197}$ which has a single amino acid change from the active diphtheria toxin and is immunologically indistinguishable from it is a component of a *Haemophilus influenzae* conjugate vaccine which has been widely used in infants.

A culture of *Corynebacterium diphtheria* strain C7 (β197), which produces $CRM_{197}$ protein, is deposited with the American Type Culture Collection, 10801 University Boulevard, Manassas, Va. 20110-2209 (accession number ATCC 53281).

Fragments of proteins may also be used for conjugating to GASP provided they are of sufficient length, i.e. preferably at least 10 amino acids to define a T-cell epitope.

Numerous methods of conjugation may be employed to create the group A polysaccharide-protein conjugate of this invention. Preferably the method used would be one which preserves the immunogenicity of the bactericidal epitope present on the β-D-GlcpNAc branches which are glycosidically linked to position 3 of rhamnose. When a single GASP bonds two or more protein molecules, the resulting conjugate is crossed-linked with respect to the protein. The degree of cross-linking and overall size of the conjugate molecule may be regulated by routine variation in the conditions used during the conjugation reaction which are well known to those of ordinary skill in the art. Such variations include for example, the rate of conjugation reaction and the ratio of proteins and GASP present in the reaction mixture.

Various chemical methods for conjugating polysaccharides to protein are known and have been described in the art. For example, U.S. Pat. No. 4,644,059 which is incorporated herein by reference, describes a conjugate made using adipic acid dihydrazide (ADH) as a homodifunctional linker. U.S. Pat. No. 4,695,624, which is also incorporated herein by reference describes methods of preparing polysaccharides and conjugates by using bigeneric spacers. A survey of various methods of preparation and factors used in designing conjugates is discussed in Dick, William E. and Michel Beurret, *Contrib. Microbiol. Immunol.* (1989), Vol. 10, pp. 48-114 and is also incorporated herein by reference. The preferred method of conjugation for the GASP-protein conjugates of this invention is reductive amination as described in U.S. Pat. No. 4,356,170 which is also incorporated herein by reference. Briefly, in the preferred embodiment, the terminal reducing sugar of the GASP is reduced to open the ring by using a mild reducing agent, e.g. sodium borohydride or its equivalent.

Next, selective oxidation with sodium metaperiodate or its equivalent is used to oxidize the terminal vicinal hydroxyl groups of the previously reduced sugar moiety forming a terminal aldehyde group. This forms an activated GASP which is now capable of covalently attaching to the selected protein carrier. In another embodiment of this invention this activated GASP may also be covalently linked to a phospholipid such as phosphatidylethanolamine which are in the form of liposomes. The chemical structure of the activated GASP is as follows:

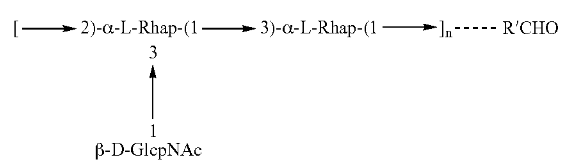

wherein R' is the product of reduction and oxidation of the terminal reducing sugar except for the portion of the terminal reducing sugar which forms the aldehyde residue (CHO). Approximately 10 mg of polysaccharide is suitably oxidized with about 1 ml of approximately 20 mM sodium metaperiodate solution for about 10-15 minutes at room temperature. The reaction time can be varied to accommodate other amounts of periodate to obtain equivalent oxidation. Reduction and opening of the terminal reducing sugar causes the vicinal hydroxyl groups on the reducing sugar to be much more reactive than those present on the glycosidically linked β-D-GlcpNAc branches. However, additional linkage sites may occur as well through the oxidation of some of the glycosidically linked β-D-GlcpNAc residues. The activated GASP and the selected conjugating protein are then conjugated in the presence of cyanoborohydrate ions, or another reducing agent, by coupling the amino groups of the carrier protein to the terminal aldehyde groups of the GASP. The group A polysaccharide and the protein are thereby linked through a $—CH_2—NH—$ protein linkage as in formula II.

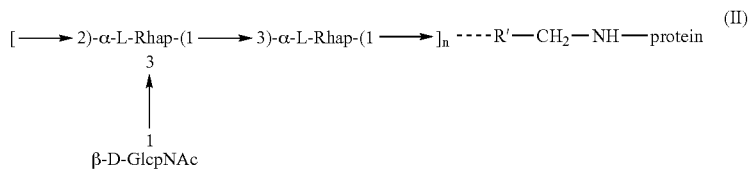

The resulting GASP-protein conjugates from the reductive amination process preferably have limited cross-linking and are preferably soluble in aqueous solutions. This makes the GASP-protein conjugate of the invention a preferred candidate for vaccine use.

In another embodiment of the invention, GASP are embedded in liposomes forming an immunogenic composition. Liposomes are often used in conjugates due to their ability for inducing a "capping" effect on B-lymphocytes. Without being bound by theory, the GASP-liposome conjugates are believed to increase antibody titers through capping thereby activating B-cell lymphocytes. The capping phenomena is well known in the field of cellular biology. Briefly, due to the liposomal structural features, liposomes are capable of being embedded with an antigen, thereby creating multivalent immunogenic structures. Since receptor molecules in the cell membrane of liposomes are mobile many of these receptors can be cross-linked by divalent reagents to form areas of two-dimensional precipitation or "patches". These patches will coalesce or cluster at the polar ends of B-cell lymphocytes forming a cap in the cell membrane of the lymphocyte. This act of antigen capping to B-cell lymphocytes if done in the presence of effector T-Helper cells will activate antibody production by the B-cell lymphocytes.

Various methods for conjugating polysaccharides to liposomes are known and have been described in the art. For example, U.S. Pat. No. 5,283,185 which is incorporated herein by reference, describes the transfer of nucleic acids into cells by preparing a mixed lipid dispersion of a cationic lipid with a co-lipid and then introducing nucleic acids into the dispersion forming a complex. Cells are then treated with this complex. In a preferred embodiment of this invention, liposomes are produced by dispersing a lipid in an aqueous solution by either injection through a fine needle or preferably by sonication as described in Fillit, H. M. Milan Blake, Christa MacDonald and Maclyn McCarty (1988), Immunogenicity of liposome-bound hyaluronate in mice, J. Exp. Med. 168: 971-982, which is incorporated herein by reference.

To prepare a liposomes containing phospholipid covalently linked to the GASP component, liposomes are formed by known methods. For example, in one embodiment of this invention phosphatidylethanolamine is dissolved in a solvent such as chloroform and added to a vessel. The chloroform solvent is removed thereby coating the vessel with phosphatidyl ethanolamine. An aqueous buffer such as water or phosphate buffered saline (PBS) is an added to the vessel and the mixture is sonicated to form liposomes. GASP which has been activated preferably by reduction followed by oxidation is then added to the liposomes in an equal molar amount and the two components are mixed overnight in the presence of any suitable buffer such as saline, Ringer's solution or most preferably phosphate buffered saline (PBS). Sodium cyanoborohydride is then added to the mixture to form the stable covalent linkage between the phosphatidylethanolamine and the GASP polysaccharide. The final product as shown in Formula III may be separated from the sodium cyanoborohydride by centrifugation, molecular seive chromatography or dialysis.

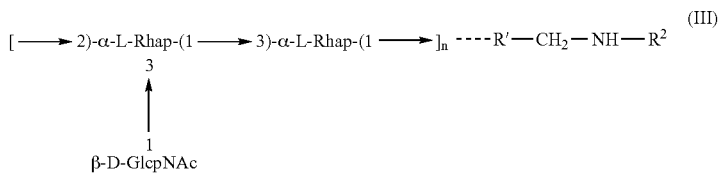

R' and n in formula III are as previously described and $R^2$ is phosphatidylethanolamine.

In a preferred embodiment the GASP-liposomes are combined with protein to incorporate hydrophobic protein into the liposomes. According to one method, the GASP-liposomes are solubilized in a 5% solution of β-octylglucoside. The protein to be added to the liposome is also solubilized in 5% β-octylglucoside and the protein and liposomes are combined. After mixing to incorporate the protein into liposome, the β-octylglucoside is removed by dialysis. The resulting GASP-liposome-protein complex may then be used as an immunogen or vaccine.

GASP may also be linked to phospholipids using other less preferred techniques such as by using benzoquinone as described in Fillit, H. M., M. McCarty, and M. S. Blake (1986), the induction of antibodies to hyaluronic acid by immunization of rabbits with encapsulated streptococci. J. Exp. Med. 164: 762-776, which is incorporated herein by reference. However, the use of such reagents may not be desirable if the composition is to be used as a vaccine.

The immunogenic compositions of the invention may be used as a means for raising antibodies useful for prophylactic and diagnostic purposes. Diagnostics are particularly useful in monitoring and detecting various infections and disease caused by group A Streptococci. Another embodiment of the invention uses the immunogenic compositions as an immunogen for use in both active and passive immunogenic protection in those individuals at risk of contacting group A Streptococcal infections or disease. The immunogenic antibodies used for passive protection are produced by immunizing a mammal with any of the immunogenic composition of the invention and then recovering the bactericidal antibodies in a gamma globulin fraction or as serum, or as specific antibodies from the mammals. As used herein, the vaccines of this invention are capable of eliciting antibodies useful or providing protection against infection of group A Streptococcal bacteria.

Additionally, the group A polysaccharide may be used on its own as an immunizing agent preferably associated with an adjuvant such as aluminum hydroxide, aluminum phosphate, monophosphoryl lipid A, QS21 or stearyl tyrosine. A further embodiment of the invention is to use the immunogenic compositions as immunogenic protection against infection by group A *Streptococcus*. In particular, this invention would provide protection for those populations most at risk of contracting group A Streptococcal infections and disease namely adults, pregnant women and in particular infants and children.

The immunogenic composition and vaccines of the invention are typically formed by dispersing the GASP or conjugate in a suitable pharmaceutically acceptable carrier, such as physiological saline, phosphate buffered saline or other injectable liquids. The vaccine is administered parenterally, for example subcutaneously, intraperitoneally, or intramuscularly. Additives customary in vaccines may also be present, for example stabilizers such as lactose or sorbitol and adjuvants such as aluminum phosphate, aluminum hydroxide, aluminum sulphate, monophosphoryl lipid A, QS21 or stearyl tyrosine.

The dose of immunogenic compositions will be that which will elicit immunogenically effective results. Dosages will normally be within the range of about 0.01 µg to about 10 µg per kilogram of body weight. A series of doses may be given for optimum immunity. Dosage unit forms of the vaccine can be provided with amounts of GASP or conjugate equivalent to from about 0.01 µg to about 10 µg micrograms.

The invention is illustrated by the following non-limiting examples.

EXAMPLE 1

The methods for growth, preparation and assay for group A Streptococcal carbohydrate antibodies and their use as a novel vaccine in adults and children are enumerated as follows:

Growth of group A *Streptococcus*

A −70° C. seed stock of group A *Streptococcus* was streaked onto a medium plate which contains 3 g/L Todd Hewitt Broth and 3 g/L yeast extract (GAS medium). The plate was incubated at 37° C. for 48 hrs., at which time, colonies (8-9) were transferred to a 200 ml GAS medium shake flask and grown for 18 hrs. at 37° C. and 120 rpm. The seed culture (150 ml) was transferred to a 15 L fermentor (New Brunswick, BioFlo 4) in Todd Hewitt Broth. The culture is grown for 7-8 hrs. at pH 7.0 and 37° C. Glucose was added at 3 g/L when the culture reaches a stationary phase (optical density at 600 nm around 1.5). The culture was allowed to grow for an additional 8 hrs. and harvested. The final optical density is approximately 2.7 at 600 nm.

Preparation of group A Streptococcal Polysaccharide

Sixty grams of group A streptococcal cells in 600 ml water were combined with 75 ml of 4 N sodium nitrite and 75 ml of glacial acetic acid. The solution was mixed for 15 minutes and centrifuged for 10 minutes at 11,000 rpm in a SS34 rotor. The supernatant was removed, dialyzed against water and lyophilized. The group A polysaccharide was purified from the crude lyophilized extract by gel filtration through a SEPHADEX G-50 column (Pharmacia) using PBS as eluant. Fractions eluting from the column were monitored for the presence of carbohydrate using the phenolsulfuric acid assay of Dubois (31). The carbohydrate positive fractions were pooled, dialyzed at 40° C. against water and lyophilized. The polysaccharide preparation (240 mg) contained less than 1% (w/w) proteins and nucleic acids. Its purity was further confirmed by $^1$H-NMR at 500 MHz using an AM-500 BRUKER spectrometer.

Preparation of Liposomes: Group A Streptococcal carbohydrate was isolated by methods previously described by McCarty (28). The lyophilized material was resuspended, adjusted to 10 mg/ml and covalently linked to liposomes using methods previously described by Fillit et al. (18) using benzoquinone as a linking agent which is incorporated herein by reference for Streptococcal hyaluronate. Briefly, GASP is reacted with benzoquinone to form an activated intermediate. This intermediate is then further reacted with phosphatidylethanolamine in the form of liposome to form the immunogenic GASP-liposome conjugate.

ELISA Assays: The ELISA method was essentially that described by Fillit et al (18) with the following modifications. Preliminary testing with human sera indicated that 0.5 µg CHO/ml in PBS, pH 7.2 of the liposomal preparation to sensitize the microtiter plates give the best results with minimal background readings against the liposomal control preparations. Accordingly, 100 µl of the preparation is placed per well in microtiter plates (Dynatech plates, USA) and incubated at 37° C. overnight. The plates were then washed 3× in ELISA wash buffer (10 mM NaAcetate, 100 mM NaCl, 0.1% BRIJ 35, pH 8.0). The human sera was diluted in the same ELISA buffer and 100 µl of a given serum dilution was placed in the plates and incubated 1 hour at 37° C. All sera were run in duplicate. After appropriate washes, 1:1,000 dilution of Goat F(ab')2 anti-human IgG (gamma chain specific) or IgM (Mu chain specific), alkaline phosphatase conjugate (Tago, Inc.,USA) was used as the secondary antibody and incubated for an additional hour at 37° C. After 3 additional washes in ELISA buffer, a phosphatase substrate (Sigma 104) in 0.1 M Diethanolamine, pH 9.6 was added to the wells, the plates incubated at 37° C. for 1 hour and read on ELIDA V (Physica Co.) instrument at 405 nm. The titer was reported as that dilution which gave a reading of 1.0.

Bactericidal Assays: The indirect bactericidal assay described by Lancefield (15,25,26) was performed as follows: Organisms of the various strains are grown for 18 hrs. at 37° C. in Todd Hewitt broth. A sample of the overnight culture was first diluted 1:2 in fresh Todd Hewitt broth and grown for an addition 2 hours at 37° C. The suspension was diluted to 1:100 followed by serial two fold dilutions in order to deliver between 5-15 colonies in 50 µl of Todd Hewitt broth. Heparinized blood was used for the source of human phagocytes. In order to avoid the presence of autologous plasma in the phagocytic suspension, the blood was centrifuged at 2,000 rpm for 10 minutes, the plasma was removed, the pellet is washed 3× in PBS (pH 7.2) and finally resuspended with RPMI (Gibco-BRL, Co., Rockville, Md.) to the same volume as the original blood sample. Complement was supplied to the assay system by using freshly isolated serum from a normal donor known to contain low amounts of anticarbohydrate antibody and which had been repeatedly absorbed at 0° C. with group A Streptococci and stored in aliquots at −70° C. (29). Prior to use, this source of complement was analyzed for both complement activity and the absence of group A carbohydrate antibodies. The bactericidal assay was performed in duplicate in sealed tubes. The reaction mixture was as follows: 300 μl of human phagocytes suspended in RPMI, 100 μl human complement, 200 μl of the serum to be tested, and 50 111 of the diluted streptococcal culture. As in the Lancefield assay, one of the duplicate tubes was rotated end over end for 3 hours at 37° C. and the second tube, which serves as a control, remains stationary at the same temperature. After 3 hours, 100 μl of each tube was plated on blood agar pour plates and incubated overnight at 37° C. The number of colonies on each plate was then counted. The opsonophagocytic activity was calculated as the percent of streptococcal killing of a particular serum by the following equation: (1-cfu in test rotated serum/cfu in stationary tube)×100.

Absorption of N-acetylglucosamine antibodies from human sera: 600 μl of a 50% suspension of a N-acetylglucosamine coupled to SEPHAROSE beads (Sigma Chemical Co.) in PBS was placed into a sterile EPPENDORF tube and centrifuged at 4° C. at 14,000 RPM for 10 minutes. The supernatant was removed and 300 μl of serum added to the beads. The suspension was rotated end over end for 1 hour at 37° C. Following a second centrifugation under the same conditions, the absorbed serum was removed and used in the bactericidal assay as described previously. To remove the N-acetylglucosamine antibodies from the affinity column, the beads containing the absorbed antibodies were packed in a 1 ml tuberculin syringe over which a solution of 0.5 8% (v/v) glacial acetic acid in 0.15 M NaCl, pH 2.2 is passed. The eluant is monitored by absorption at 280 nm and the peak fractions collected, dialyzed against PBS, pH 7.2, and concentrated back to the original volume of serum using an Amicon CENTRIPREP 30 concentrator (Amicon, Beverly, Mass.).

Human Sera: Individuals included in this study were from Trinidad, New York City, and the Great Lakes Naval Training Station. Their ages ranged from 5-20 yrs. Blood was obtained by venipuncture and serum collected using standard sterile techniques. All sera were age, origin and health condition matched as shown in Table I.

TABLE I

Population Distribution

| Patients | Age (Years) | No. of Patients |
|---|---|---|
| Normal Children - Trinidad | 5 | 36 |
| Normal Children - Trinidad | 10 | 16 |
| Normal Children - New York | 5 | 32 |
| Normal Children - New York | 10 | 22 |
| Rheumatic Fever - Trinidad | 7 | 19 |
| Nephritis - Trinidad | 4 | 18 |
| Uncomplicated Scarlet Fever | 18-20 | 6 |
| Complicated Scarlet Fever (ARF) | 18-20 | 5 |

Bactericidal Assays: Having established that human sera do contain group A carbohydrate antibodies and that the titers of these antibodies do vaty in individuals, we next addressed the question of whether these antibodies would also promote opsonophagocytosis in an in vitro assay system. The bactericidal assay was essentially that used by Dr. Lancefield (15,25,26) for testing human sera with the modifications as outlined above. FIG. 4 is illustrative of the results of the phagocytic assays. Using an inoculum of nine colony forming units of a serotype 6 group A Streptococcal strain, there was a marked increase in the number of colonies in the rotated tubes in the presence of normal rabbit serum (FIG. 4A). FIG. 4B shows a slight increase in the stationary tube in which the human serum was used. In marked contrast, the rotated tube containing the human serum (FIG. 4C) completely abolished the growth of the organisms (compare FIGS. 4B and 4C).

Figure 5:
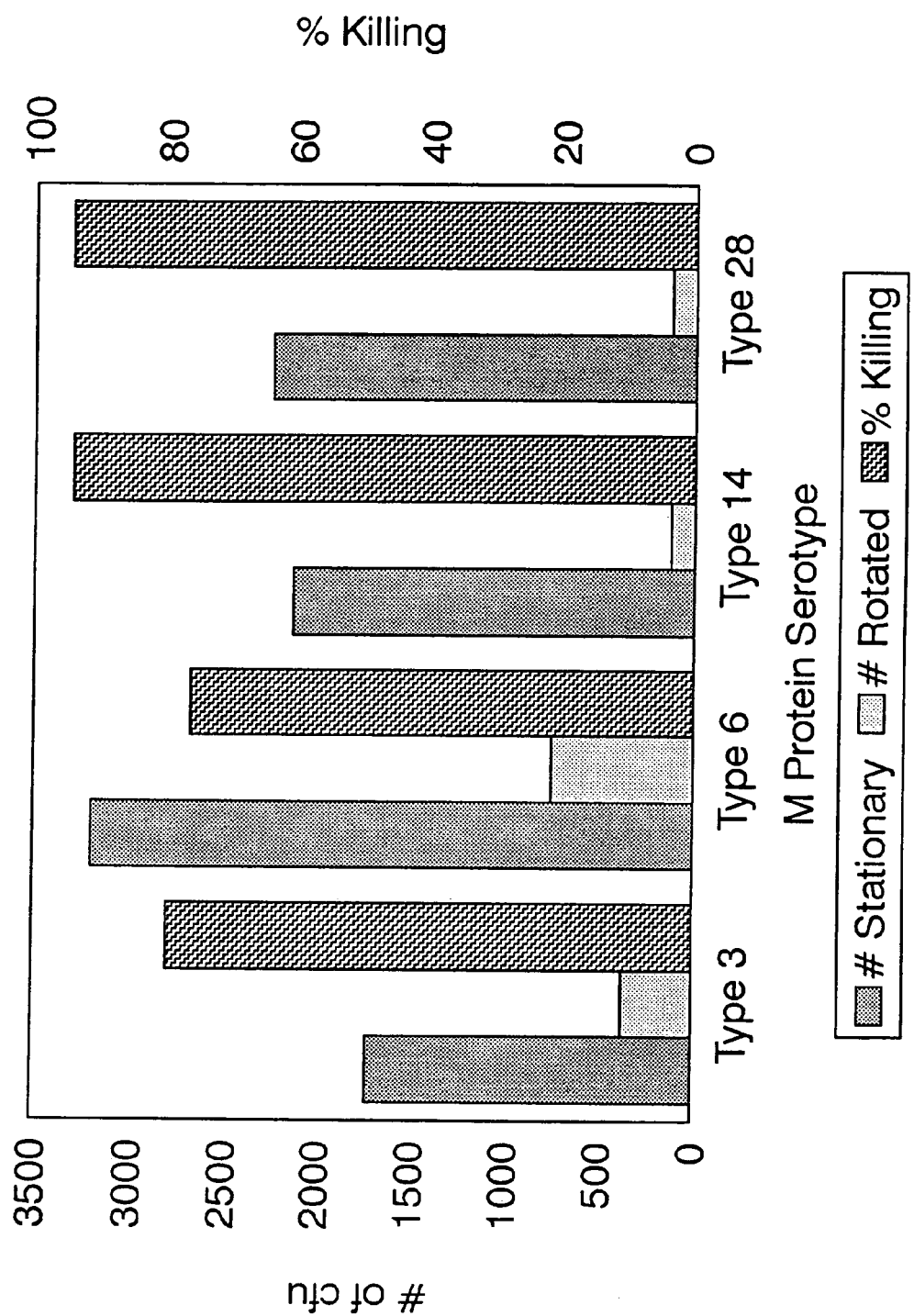
FIG. 5 graphically illustrates the indirect bactericidal assays as described in FIG. 4. The organisms were a serotype 3 (strain D58/11/3), a serotype 6 (strain S43), a serotype 14 (strain S23/101/5), and a serotype 28 (strain T28/isoA/5). The left axis depicts the number of colony forming units in the rotated verses the stationary tubes. The right axis denotes the percentage in killing of the organisms in the rotated versus the stationary tubes.

To be sure that the observed opsonophagocytosis of group A Streptococci was not limited to one serotype, these experiments were repeated using three other group A strains of differing M protein serotypes. As seen in FIG. 5, all of the other three strains were phagocytosed in the presence of human sera in a manner similar to that observed for the type 6 strain. The percentage of killing varied for 80-100% when the rotated versus stationary tubes were compared. The serotype 3, 14, 28 strains are the identical strains utilized by Dr. Lancefield in her phagocytic assays (15,25,26).

Figure 7:
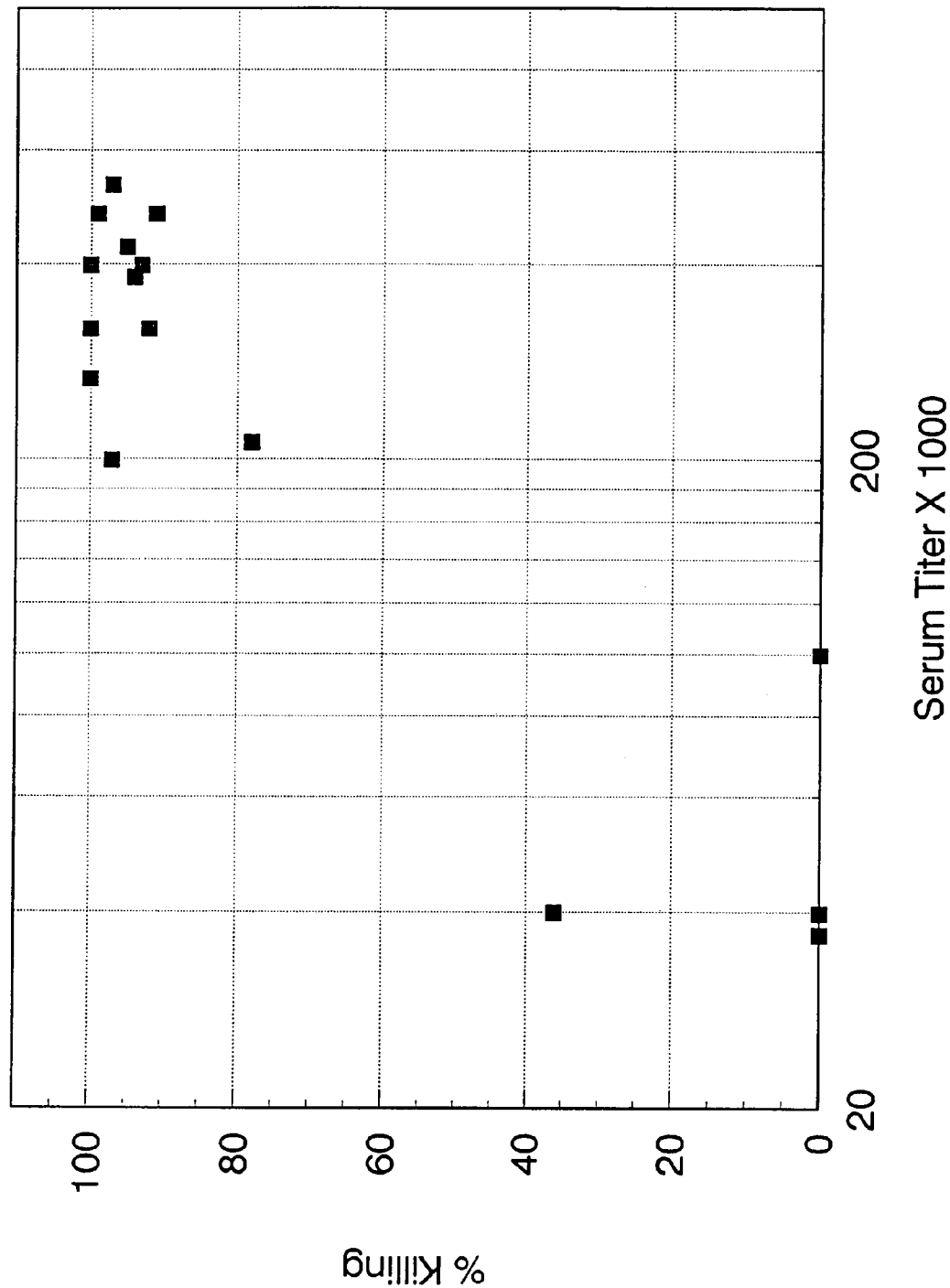
FIG. 7 graphically illustrates bactericidal assays of anti-group A assays carbohydrate titers as measured in the ELISA assay. 17 individual human sera were tested in both assays using the serotype 6 organisms. Note that all sera (13/13) exhibiting a carbohydrate (CHO) titer greater than 200,000 exhibit greater than 80% killing in the bactericidal assay. In contrast, only one out of 4 sera with titers less than 200,000 promoted opsonophagocytosis of the organisms and the degree of phagocytosis was much less than that observed with sera of higher titer.
Figure 8:
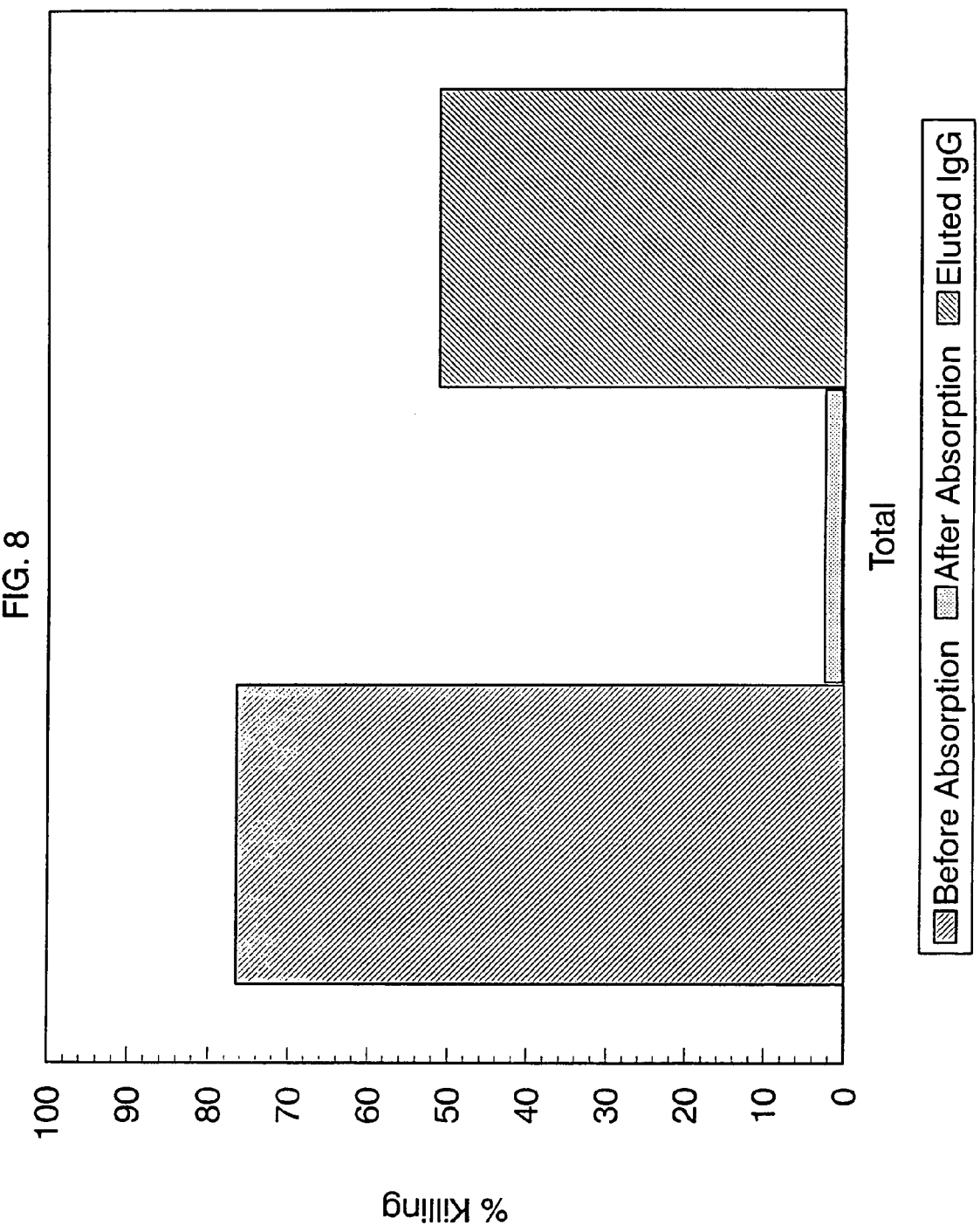
FIG. 8 graphically illustrates opsonophagocytic bactericidal assays as described in Example 1. Phagocytosis of the organisms is depicted in percentage of killing of the organism compared to the stationary controls. Bars indicate percent killing before adsorption with the N-acetylglucosamine affinity column, after absorption with the affinity column, and percent killing of antibodies eluted from the column. Note the complete absence of killing of all sera after absorption with the N-acetylglucosamine affinity column and the partial recovery of the opsonophagocytic bactericidal activity after elution of the antibodies from the affinity column. The standard error is shown in each case except in the absorbed sera where there was a complete lack of killing.

Relationship between the Anti-CHO Titers and opsonophagocytosis by human sera: Employing the phagocytic assay, it is clear that human sera differed in their ability to promote phagocytosis of group A Streptococci. In general the phagocytic properties of a given serum correlated with the titers of the antigroup A carbohydrate antibodies. As seen in FIG. 7, all sera exhibiting titers greater than 200,000 exhibited greater than 80% killing, while three out of the four sera with titers less than 200,000 did not. One serum with a CHO titer of 40,000 did promote phagocytosis but the degree of killing was far less than that observed with high titered anti-CHO sera.

Studies of phagocytosis by human sera in heparinized blood versus heparin free assays: Because of the known ability of heparin to bind and inactivate numerous components of complement and to correlate our phagocytic assay with those which had been previously used, the opsonophagocytic abilities of normal human sera described above were tested in phagocytic assays in the presence and absence of heparin. Heparinized human blood was drawn by venipuncture, washed extensively in PBS as described above and divided into two aliquots. One aliquot was resuspended to the original volume with RPMI and the opsonic assay was performed as described above. The second aliquot was treated in the same manner but with the addition of 5 units per ml of heparin following which the assay was carried out in the same manner as the other aliquot.

Figure 6:
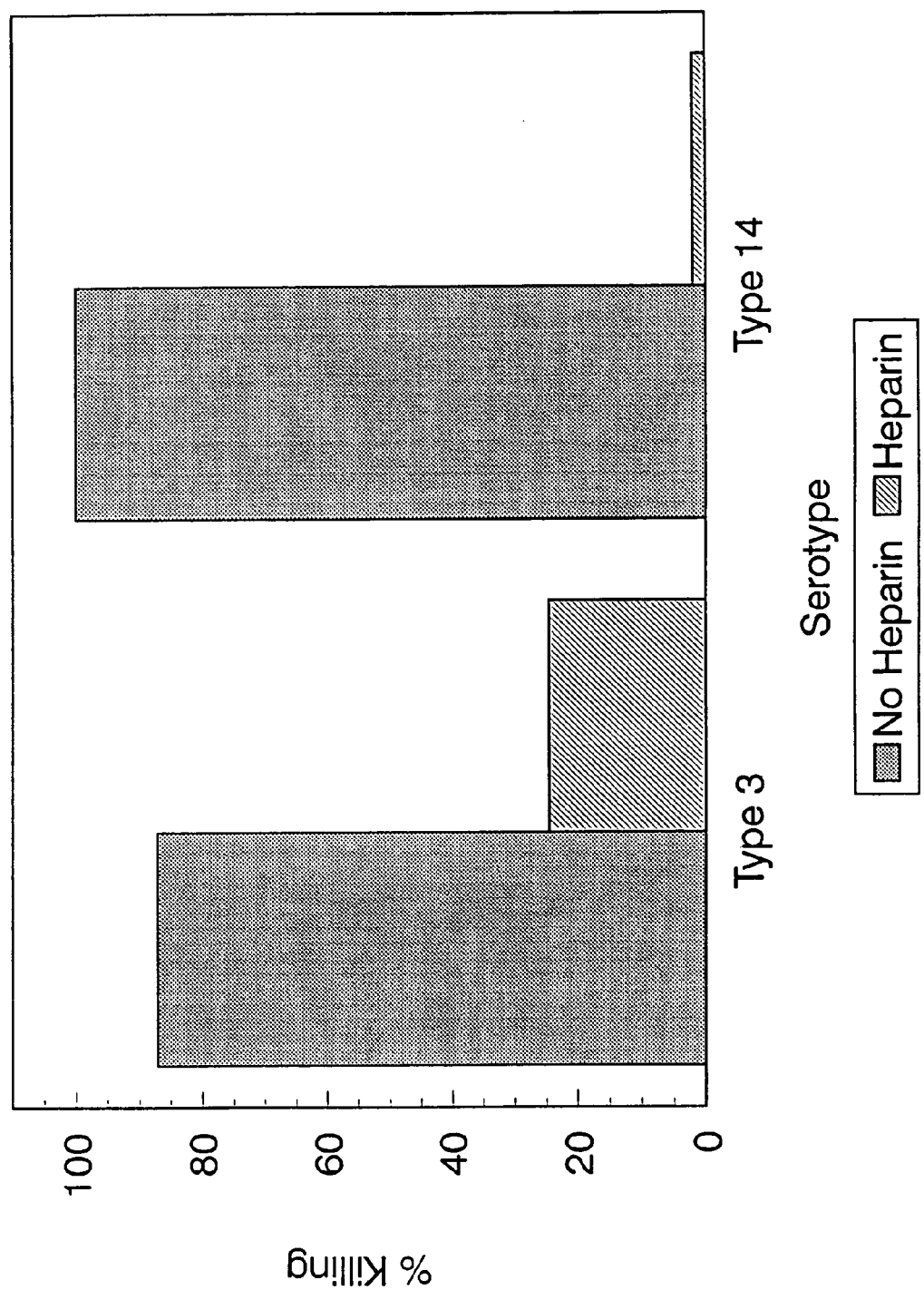
FIG. 6 graphically illustrates the effect of heparin on indirect bactericidal assays. The indirect bactericidal assay was performed as described but in duplicate. Heparin (5 units/ml) was added to one set of stationary and routed tubes, while the other set of tubes served as the normal bactericidal assay controls. The standard amount of heparin used in bactericidal assays fashioned after that described by Lancefield is 10 units/ml (33-35). As can be seen, heparin, at half the usually described concentration, drastically reduces the amount of anti-Group A carbohydrate antibody dependent killing.

The results depicted in FIG. 6 reveal that in the absence of heparin there was on average 94% phagocytosis of the Group A streptococci by the human serum. However, in the presence of heparin, the same serum was only able to achieve an average 12% phagocytosis of the same inoculum.

Figure 9:
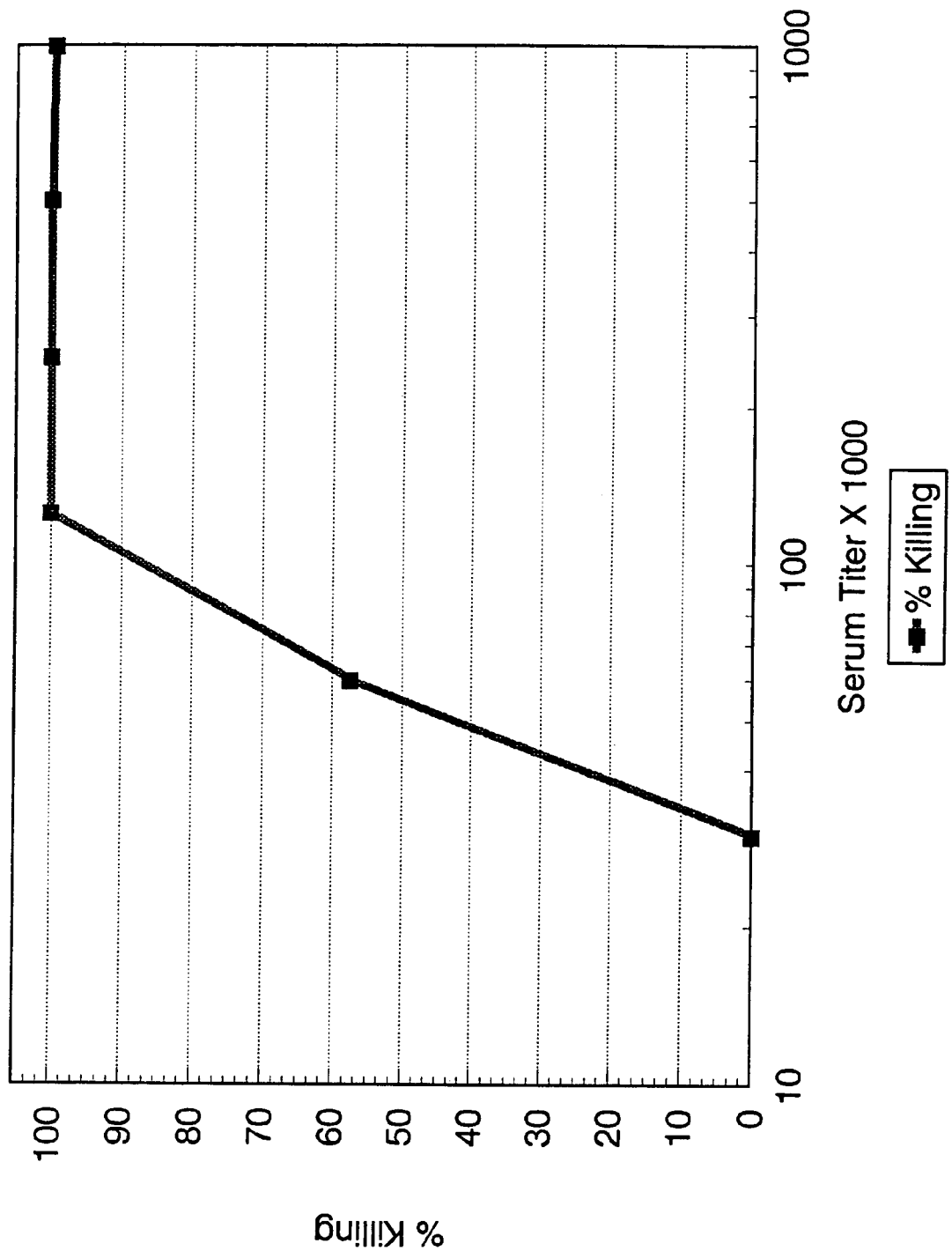
FIG. 9 graphically illustrates the opsonophagocytic index of a rabbit serum known to have high titers of anti-Gr.A carbohydrate antibodies after immunization with group A streptococcal carbohydrate. Phagocytosis of the organisms is depicted as percentage of killing of the organism compared to the stationary controls. Note the lack of phagocytosis of the organism with titers <50,000, a gradual increase in killing with titers of 75,000 and complete phagocytosis with titers above 100,000. The organism used for these studies was a group A type 6 strain and the inoculum was 4 colony forming units.

Absorption Experiments: In an effort to determine which part of the streptococcal carbohydrate moiety was responsible for the bactericidal activity, human sera were absorbed with N-acetylglucosamine coupled SEPHAROSE beads as described in the methods section. Absorbed and non-absorbed sera were then used in the standard bactericidal assay. FIG. 7 shows the results of these experiments. The unabsorbed serum clearly enhanced phagocytosis of the streptococci. In contrast, the serum absorbed with the N-acetylglucosamine coupled beads removed the opsonizing antibodies. As a viability control, normal rabbit serum did not enhance phagocytosis. These experiments indicate that the antibodies directed against the non-reducing terminal N-acetylglucosamine residue on group A carbohydrate were extremely important in the opsonophagocytosis of group A Streptococci in our bactericidal assays. To confirm these results, the antibodies from selected sera which had been absorbed to the N-acetylglucosamine affinity column were eluted and used in the bactericidal assay. As also shown in FIG. 9, these experiments demonstrated that N-acetylglucosamine specific antibodies eluted from the affinity column were capable of partially restoring the opsonophagocytic bactericidal activity of the serum.

Using methods designed to measure both precipitating and non-precipitating antibodies reactive to group A Streptococcal carbohydrate, this carbohydrate was covalently linked to phosphatidylethanolamine and incorporated into a liposome capable of binding to microtiter plates. This method clearly demonstrates that the majority of human sera contain antibodies to group A Streptococcal polysaccharide.

Surprisingly we found that children from different geographical locations exhibited marked differences in their titers to the group A carbohydrate. While the amount of streptococcal exposure (both impetigo and pharyngitis) is greater in Trinidad compared to New York, streptococcal infections are also Common in New York. In this context, Zimmerman et al. (23) did note lower group A carbohydrate antibody titers in patients being carefully monitored and treated for group A Streptococcal infections compared to a non-monitored group. Furthermore, carbohydrate antigens in general are T cell independent and it is thus conceivable that repeated exposure to the antigen is needed to elicit the antibody response.

The studies with sera obtained from patients during the acute and convalescent stages of scarlet fever suggest that the antibody titers to group A Streptococcal carbohydrate were already present at the onset of disease but did increase two-fold during the convalescence. When ARF sera following acute streptococcal infection were examined, the titers to the group A carbohydrate were lower at the time of presentation with the onset of scarlet fever compared to uncomplicated scarlet fever sera but increased four-fold at the time of presentation with ARF, suggesting perhaps a stronger immune response to the antigen compared to uncomplicated scarlet fever patients. The antibody titers to group A carbohydrate was significantly lower than those seen in scarlet fever patients who did not develop ARF. Inhibition studies with group A and group A variant carbohydrate clearly demonstrate that the majority of these antibodies are directed towards the group A specific nonreducing terminal N-acetylglucosamine residue on the group carbohydrate and not against the rhamnose backbone.

The question of whether these carbohydrate antibodies promote opsonophagocytosis of group A Streptococci has been answered affirmatively and the degree of opsonization correlated well with the level of anti-carbohydrate antibodies. ELISA titers of less than 100,000 were generally ineffective while the majority of sera with titers greater than 200,000 promoted phagocytosis. An important observation was the fact that this opsonophagocytosis was not limited to one serotype of group A Streptococci since at least three other strains of different serotypes were also phagocytized. The importance of the role of the N-acetylglucosamine reactive antibodies in opsonization was attested to by the fact that the absorption of these antibodies from human sera completely abolished the bactericidal activity of the sera and that, when these antibodies were eluted and added back to the bactericidal assays, killing was restored.

Several observations concerning the kinetics of the bactericidal assay with human sera are worthy of comment. First, only small inocula of streptococci in the bactericidal assay were effective while larger inocula often overwhelmed the ability of human sera to opsonize the organisms. Secondly, the bactericidal activity primarily worked with undiluted sera in a manner similar to that observed by Dr. Lancefield in her studies of human sera and type specific antibodies (15,25,26). In contrast, animal sera immunized with a given type specific protein were effective even at dilutions of 1:20 or more.

EXAMPLE 2

Comparison of group A carbohydrate reactive antibody titers in normal children: Our first efforts were directed towards determining whether or not normal children developed antibodies to group A Streptococcal carbohydrate and if the titer of these antibodies varied with the individual's age and the geographical area in which the individual lived. Accordingly, the group A carbohydrate reactive antibody titers were measured on sera obtained from normal 5 and 10 year olds in Trinidad (high streptococcal exposure) and compared with age matched children in New York (low streptococcal exposure) using the ELISA assay described in the materials and methods section. FIG. 2 illustrates that by the age of 5 years, 94% of the children from Trinidad exhibited antibody titers less than 1:10,000 with an average antibody titer of 1:158,472. These antibody titers were not significantly different from the sera of children tested at 10 years of age. In contrast, 5 year old children in the New York area exhibited significantly lower titers with an average of 1:6,100 which increased to 1:25,500 by the age of 10 years. Titers of children in the New York area in both age groups were clearly lower than the corresponding titers of children in Trinidad as demonstrated by the fact that 69% of the New York children had titers greater than 1:10,000.

In order to determine whether the immune response to the group A carbohydrate was either of the IgG or IgM class, the following experiment was performed. Selected sera exhibiting high titers to the group A carbohydrate were appropriately diluted so that each serum gave a reading of 1.0 at 405 nm in the ELISA assay. Each serum was then tested with either affinity purified human anti-IgG or anti-IgM alkaline phosphatase conjugate secondary antibody. As seen in Table II the majority of the antibody detected against the streptococcal carbohydrate was of the IgG class and only minimal reactions were seen in the IgM class.

TABLE II

ELISA Determinations of IgG and IgM Antibody Titers to the *Streptococcal* CHO-Liposome Complex

| Patient | Immunoglobulin Class | |
| --- | --- | --- |
| | IgG | IgM |
| 1 | 1,200,000 | 6000 |
| 2 | 640,000 | 2000 |
| 3 | 480,000 | 2000 |
| 4 | 360,000 | 2000 |
| 5 | 320,000 | 1000 |

Each serum was appropriately diluted to give a reading of 1.0 optical density at 405 nm in the ELIDA V reader.

EXAMPLE 3

Figure 3:
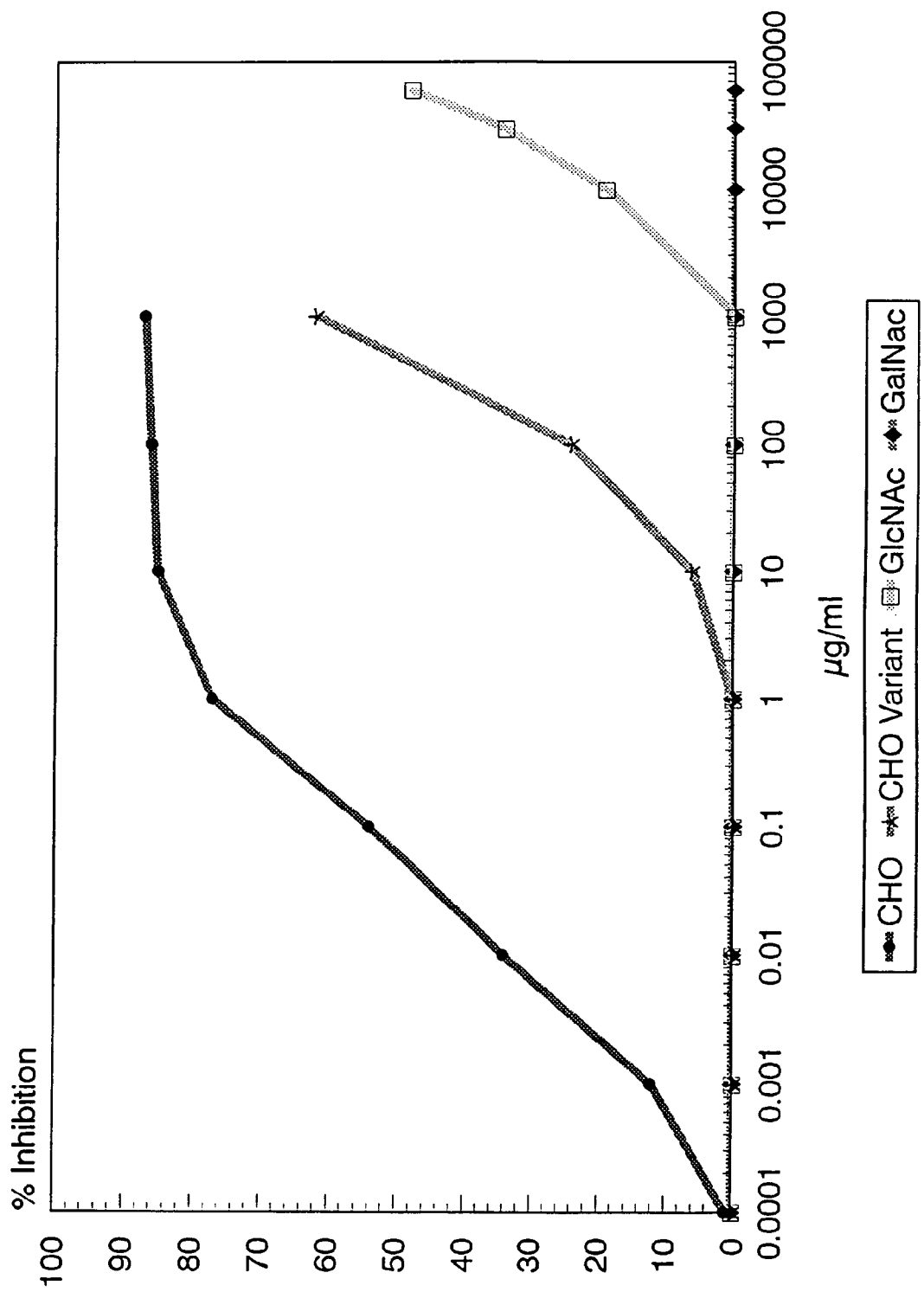
FIG. 3 graphically illustrates the inhibition ELISA studies with human sera known to have antibodies reactive to the Group A-liposomes. The sera were appropriately diluted to give a value of 1.0 OD units at 405 nm and mixed with varying concentrations of different antigens for 1 hr at 37° C., centrifuged for 5 min at 10,000 rpm. The supernatants were tested for reactivity in the ELISA assay as described in Example 3. The data represents the average of sera tested.

Partial structural determination of the group A reactive antibodies: Zimmerman et al (23) had previously demonstrated that some human sera contained antibodies reactive with the group carbohydrate isolated from group A variant streptococci and thus were directed at the poly-rhamnose backbone portion of the group A polysaccharide molecule. To determine the amount of these rhamnose-backbone reactive antibodies in comparison with antibodies reactive to the terminal N-acetylglucosamine group A determinant in individual serum, inhibition studies of normal sera using both group A and group A variant purified carbohydrates were performed. As before, the group A carbohydrate liposome complex was used to sensitize microtiter plates. A 100 µl of the appropriate serum was mixed with varying concentrations of carbohydrate and incubated for 1 hour in a 37° C. water bath. The mixture was then centrifuged at 10,000 RPM for 5 minutes and the supernatant reacted in the ELISA assay. Controls included the serum mixed with saline. As shown in FIG. 3, the majority of the antigroup A carbohydrate reactive antibody in normal sera was directed against the group A carbohydrate moiety, i.e. the N-acetylglucosamine determinant. Some inhibition was observed with the A variant carbohydrate but the amount needed to achieve the same degree of inhibition was 1,000-5,000 times greater than the group A carbohydrate. Since group A variant carbohydrate is contaminated with approximately 4% N-acetylglucosamine (compared to 36% for group A carbohydrate), some of the detected inhibition could be reactive with the remaining N-acetylglucosamine. This showed that the majority of the immunoreactivity of the sera was directed at the N-acetylglucosamine moiety which can be seen by the loss of group A antibody reactivity in the ELISA assay by the addition of purified N-acetylglucosamine (Sigma). This can be directly compared with the lack of any inhibition by the addition of the closely related monosaccharide N-acetyl galactosamine.

EXAMPLE 4

Comparison of anti-group A carbohydrate antibody titers in ARF versus APSGN patients: To determine if anti-group A carbohydrate antibody titers differed in patients with well documented post streptococcal sequelae, serum samples obtained from acute rheumatic fever patients (ARF) were compared to sera obtained from acute post streptococcal glomerulonephritis patients (APSGN). All sera were obtained from well documented ARF and AGN patients hospitalized in Trinidad and were drawn prior to treatment during the acute stages of the disease. Table III summarizes the results and it can be seen that there was an increased reactivity to group A carbohydrate in the sera of APSGN patients (<50%) compared to ARF patients at onset of disease. When compared to normal children in Trinidad, there was also a significant difference in titers between these patients and the titers of normal children in Trinidad (see FIG. 2).

TABLE III

Mean Titers of Anti-Carbohydrate Antibodies in the Sera of Patients with APSGN, ARF, and Uncomplicated Scarlet Fever Great Lake Series

| Patients | Number | Average Titers at Onset | Average Titers 4 Weeks Later |
| --- | --- | --- | --- |
| Scarlet Fever | 6 | 8,838 | 18,050 |
| ARF | 5 | 2,045 | 7,950 |

Trinidad Series

| Patients | Number | Average Titers |
| --- | --- | --- |
| ARF | 19 | 202,300 |
| APSGN | 18 | 299,900 |

EXAMPLE 5

Determination of anti-group A carbohydrate antibody titers in patients with uncomplicated streptococcal infections versus ARF: Our collection of Great Lakes sera were obtained from patients all of whom had contracted scarlet fever at the Great Lakes Naval Training Station in 1946. A fraction of these patients went on to develop classical ARF. Accordingly, sera were selected from these patients as follows: 1) during the acute onset of scarlet fever, 2) during the convalescent stage of the scarlet fever (4 weeks later), or 3) during the onset of ARF (3-4 weeks) after the acute streptococcal infection. Table III demonstrates that, in a small number of cases, reactivity to the group A carbohydrate increased during the convalescent stages of disease, when compared to the onset (defined as the time of presentation with scarlet fever). These increases in antibody titer to the group A carbohydrate were seen in both the uncomplicated scarlet fever group as well as in those patients who developed ARF 4 weeks after the onset of scarlet fever. While the number of cases studied were small, it is of interest that the titers to the group A carbohydrate were lower in ARF patients both at the onset of scarlet fever and at onset of rheumatic fever 4 weeks later when compared to the uncomplicated scarlet fever cases.

EXAMPLE 6

Group A Polysaccharide—Protein Conjugates

A. $NaBH_4$ Reduction of the Reducing Termini of Group A Polysaccharide

Purified group A polysaccharide (GPSP) (100 mg) was dissolved in 10 ml water and the pH of the solution was adjusted to 10 with 0.5 N NaOH. Solid $NaBH_4$ (100 mg) was added to the solution and following incubation of the reaction mixture at room temperature for two hours, the excess borohydride was destroyed with 1 M AcOH. The solution was dialyzed against water in the cold and lyophilized, affording 91 mg of reduced GASP.

B. Introduction of a Terminal Aldehyde in the Group A Polysaccharide by Controlled Periodate Oxidation The reduced GASP (90 mg) was dissolved in 4.5 ml of water and then combined with 4.5 ml of 50 mM $NaIO_4$. After 30 min. at room temperature, the excess periodate was destroyed by the addition of 1 ml ethylene glycol and the solution was dialyzed against water in the cold and lyophilized, affording 73 mg of oxidized GASP.

C. GASP-TT and GASP-HSA Conjugates

The oxidized GASP was linked to either monomeric tetanus toxoid (TT) (SSI, Copenhagen, Denmark) or human serum albumin (HSA) (Sigma) by reductive amination with $NaBH_3CN$.

Oxidized GASP (40 mg) and either monomeric TT (20 mg) or HSA (20 mg) were dissolved in 0.2 M phosphate buffer pH 7.4 (0.7 ml). Following the addition of $NaBH_3$ CN (20 mg), the reaction mixture was incubated at 37° C. for 4 days. The progress of the conjugation was monitored by HPLC of small aliquots of the reaction mixture analyzed on Superose-12 (Pharmacia). The conjugates were purified by chromatography on a column of Superdex G-200 (Pharmacia) using PBS as an eluant. Fractions eluting from the column were monitored by a Waters R403 differential refractometer and by U.V. Spectroscopy at 280 nm. The fractions containing the group A polysaccharide-conjugates were pooled, dialyzed and lyophilized. The protein content of the conjugates was estimated by the method of Bradford (Bradford, M. M., 1976. Anal. Biochem. 72: 248-254) with human serum albumin as a standard. The carbohydrate content was measured by the method of Dubois et al. (31)

with purified GASP as a standard. The TT conjugate contained 39% (w/w) carbohydrate and 61% (w/w) protein. Assuming an average molecular weight of 10,000 kilodaltons for the polysaccharide (as determined by HPLC on Superose-12 using dextrans as molecular weight markers and as measured by laser scattering as molecular weight markers) and a molecular weight of 150,000 kilodaltons for the monomeric TT, the GASP-TT conjugate had a molar ratio of polysaccharide to TT of 9-10:1 respectively.

EXAMPLE 7

Immunizations and Immunoassays
A. Immunization Procedures
A group of five New Zealand, white, female rabbits (7-8 weeks old) were vaccinated subcutaneously at two sites on the back (three times at three week intervals) with 10 mcg of either uncoupled native group A polysaccharide or as -TT conjugate in a total volume of 0.5 ml. The vaccines were given either unadsorbed or adsorbed on aluminum oxyhydroxide (Alhydrogel; Superfos, Denmark) or stearyl tyrosine (ST), both a concentrations of 1.0 mg in alum or ST/ml saline. Thimerosal was added to the vaccines at a final concentration of 1/10,000. A group of five rabbits received the conjugate vaccine emulsified in complete Freund's adjuvant (Sigma Laboratories) for the first injection and in incomplete Freund for the following booster injections. Serum was collected from each animal on days 0, 21, 42, and 52.

B. ELISA
Microtiter plates (Nunc Polysorb ELISA plates) were coated with 100 ng of GASP-HSA conjugate diluted to 1.0 mcg/ml in PBS and plates were incubated at 37° C. for one hour. After coating, they were washed with PBS containing 0.05% tween 20 (PBS-T) and blocked with 0.5% BSA in PBS for one hour at room temperature. The wells were then filled with 100 µL of serial 2-fold dilutions in PBS-T of rabbit antiserum and the plates were incubated for one hour at room temperature. After washing with PBS-T, the plates were incubated for 30 minutes at room temperature with 100 µL of peroxidase-labeled goat anti-rabbit IgG (H&L) (Kirkegaard & Perry Laboratories) and then washed five times with PBS-T. Finally, 50 µL of TMB peroxidase substrate (Kirkegaard & Perry Laboratories) were added to each well and following incubation of the plates for 10 min. at room temperature, the reaction was stopped by the addition of 50 µL of 1 M $H_3PO_4$. The plates were read at 450 mn with a Molecular Devices $E_{max}$ microplate reader using 650 nm as a reference wave length (see Table IV).

While we have herein before described a number of embodiments of this invention, it is apparent that the basic constructions can be altered to provide other embodiments which utilize the methods of this invention. Therefore, it will be appreciated that the scope of this invention is defined by the claims appended hereto rather than by the specific embodiments which have been presented herein before by way of example.

TABLE IV

GAS polysaccharide - specific antibody titers of rabbits vaccinated with GAS polysaccharide or GAS polysaccharide - Tetanus toxoid conjugate in various formulations.

| | Antibody titer in ELISA AT day* | | | |
|---|---|---|---|---|
| Vaccine | 0 | 21 | 42 | 52 |
| GASP (Saline) | 100 | 100 | 100 | 100 |
| GASP-TT (Saline) | 100 | 100 | 4,130 (900-12,000) | 7,600 (2,600-13,500) |
| GASP-TT (Al(OH)$_3$) | 100 | 10,600 (4,800-21,000) | 81,800 (51,000-129,000) | 141,800 (76,700-287,500) |
| GASP-TT (ST) | 100 | 6,200 (2,300-12,700) | 21,100 (8,300-31,000) | 59,600 (21,300-95,500) |
| GASP-TT (CFA, IFA) | 100 | 188,000 (2,200-428,500) | 1,664,000 (1,000,000-2,299,000) | 1,760,000 (1,100,000-2,370,000) |

*Geometric mean titer (range) with a value of 100 indicating an antibody titer of ≦100. Values are the means of duplicate determinations. Rabbits (groups of 5 NZW) were injected S.C. with 100 mcg of polysaccharide (native or conjugated) at day 0, 21, and 42.

REFERENCES CITED

1. Powers, G. F. and P. L. Boisvert. (1944). Age as a factor in streptococcosis. J. Pediat. 25: 481.
2. Paul, J. R. (1957). The Epidemiology of Rheumatic Fever. Anonymous, editor. American Heart Association, New York, N.Y. 19-21.
3. Zingher, A. (1924). The Dick test in normal persons and in acute and convalescent cases of scarlet fever. J. Amer. Med. Ass. 83: 432.
4. Goldschneider, I., E. C. Gotschlich, and M. S. Artenstein, (1969). Human immunity to the meningococcus. I. The role of humoral antibodies. J. Exp. Med. 129: 1307-1326.
5. Fothergill, L. D. and J. Wright, (1933). Influenzal meningitis: The relation of age incidence to the bactericidal power of blood against the causal organism. J. Immunol. 24: 273.
6. Schick, B. (1942). Brennenmenn's Practice of Pediatrics, Anonymous, editor. W. F. Prior Co. Inc., Hagarstown, Md.
7. Aycock, W. L. and S. D. Kramer, (1930). Immunity to poliomyelitis in normal individuals in urban and rural communities as indicated by neutralization test. J. Prev. Med. 4: 189.

8. Stokes, J., Jr. (1959). Mumps. In Textbook of Pediatrics. W. E. Nelson, editor. W. B. Saunders Co., Philadelphia, Pa. 505.
9. Dochez, A. R., O. T. Avery, and R. C. Lancefield, (1919). Studies on the biology of *Streptococcus*. I. Antigenic relationship between strains of *streptococcus* hemolyticus. *J. Exp. Med.* 30: 179-213.
10. Lancefield, R. C. (1933). A serological differentiation of human and other groups of haemolytic streptococci. *J. Exp. Med.* 57: 571-595.
11. Lancefield, R. C. (1962). Current knowledge of type specific M antigens of group A Streptococci. *J. Immunol.* 89: 307-313.
12. McCarty, M. (1956). Variation in the group specific carbohydrate of group A Streptococci. II. Studies on the chemical basis for serological specificity of the carbohydrate. *J. Exp. Med.* 104: 629-643.
13. McCarty, M. (1971). The streptococcal cell wall. In The Harvey Lectures, H. Harris, D. E. Koshland, M. McCarty, A. B. Pardee, G. Popjak, R. R. Porter, J. E. Seegmiller, and E. R. Stadtman, editors. Academic Press, New York. 73-96.
14. Lancefield, R. C. and E. W. Todd, (1928). Antigenic differences between matt hemolytic streptococci and their glossy variants. *J. Exp. Med* 48: 769-790.
15. Lancefield, R. C. (1959). Persistence of type specific antibodies in man following infection with group A Streptococci. *J. Exp. Med.* 110: 271-292.
16. Fischetti, V. A., (1989). Streptococcal M Protein: Molecular design and biological behavior *Cin. Microbiol. Rev.* 2: 285-314.
17. Seastone, C. V. (1939). The virulence of group C streptococci of animal origin. *J. Exp. Med.* 70: 361-378.
18. Fillit, H. M., M. McCarty, and M. S. Blake. (1986). The induction of antibodies to hyaluronic acid by immunization of rabbits with encapsulated streptococci. *J. Exp. Med.* 164: 762-776.
19. Faarber, P., P. J. A. Capel, G. P. M. Rigke, G. Vierminden, L. B. A. Van de Putte, and R A. P. Koene. (1984). Cross reactivity of acute DNA antibodies with proteoglycans. *Clin. Exp. Immunol.* 55: 502-508.
20. Rotta, J. and B. Bednar, (1969). Biological properties of cell wall mucopeptides of hemolytic streptococci. *J. Exp. Med.* 130: 31-47.
21. Schmidt, W. C. and D. J. Moore, (1965). The determination of antibody to group A Streptococcal polysaccharide in human sera by agglutination. *J. Exp. Med* 121: 793-806.
22. Karakawa, W. W., C. K. Osterland, and R. M. Krause. (1965). Detection of group specific antibodies in human sera. *J. Exp. Med.* 122: 195-210.
23. Zimmerman, R. A., A. H. Auernheimer, and A. Taranta, (1971). Precipitating antibodies to group A polysaccharide in humans. *J. Immunol.* 107: 832-841.
24. Dudding, B. A. and E. M. Ayoub. (1968). Persistence of group A antibody in patients with rheumatic valvular disease. *J. Exp. Med.* 128: 1081-1092.
25. Lancefield, R. C. (1957). Differentiation of group A Streptococci with a common R antigen into three serological types, with special reference to the bactericidal test. *J. Exp. Med* 106: 525-544.
26. Lancefield, R. C. (1958). Occurrence of R antigen specific for group A type 3 Streptococci. *J. Exp. Med* 108: 329-341.
27. Gotschlich, E. C., R. Austrian, B. Cvjetanovic, and J. B. Robbins, (1978). Prospects for the prevention of bacterial meningitis with polysaccharide vaccines. *Bull. Wld Hlth. Org.* 56: 509-518.
28. McCarty, M. (1958). Further studies on the chemical basis for serological specificity of group A Streptococcal carbohydrate. *J. Exp. Med.* 108: 311-328.
29. Joiner, K. A., K. A. Warren, E. J. Brown, J. L. Swanson, and M. M. Frank, (1983). Studies on the mechanism of bacterial resistance to complement mediated killing: IV C5b-9 forms high molecular wight complexes with bacterial outer membrane constituents on serum-resistant, but not on serum-sensitive *Neisseria gonorrhoea*. *J. Immunol.* 131: 1443-1451.
30. Dubois, M., K. A. Gilles, J. K. Hamilton, P. A. Rebers and F. Smith, (1956). Colorimetric Method For the Determination of Sugars and Related Substances, *Anal. Chem.* 28: 350-356.
31. Fillit, Howard M., Milan Blake, Christa MacDonald and Maclyn McCarty, (1988). Immunogenicity of Liposome Bound Hyaluronate in Mice. *J. Exp. Med.* 168: 971-982.

We claim:

1. A method of eliciting bactericidal antibodies specific to group A streptococcal polysaccharide in a mammal comprising administering to the mammal an immunogenically effective dosage amount of a polysaccharide-protein conjugate or a polysaccharide-protein fragment conjugate comprising a polysaccharide component and a protein or a protein fragment component, wherein the polysaccharide component of said conjugate is of formula (I):

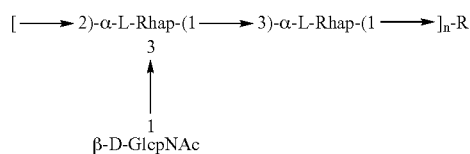

wherein R is a terminal reducing L-rhamnose or D-GlcpNAc and n is a number from 3 to 50, and wherein said polysaccharide component is covalently bound to the protein component or the protein fragment component of said conjugate.

2. The method of eliciting bactericidal antibodies specific to group A streptococcal polysaccharide according to claim 1, wherein the mammal is a human.

3. The method of eliciting bactericidal antibodies specific to group A streptococcal polysaccharide according to claim 1, wherein n is 3 to 30.

4. The method of eliciting bactericidal antibodies specific to group A streptococcal polysaccharide according to claim 2, wherein the polysaccharide component has a molecular weight of about 10 kilodaltons.

5. The method of eliciting bactericidal antibodies specific to group A streptococcal polysaccharide according to claim 2, wherein the protein component is bound to the polysaccharide component through a secondary amine bond.

6. The method of eliciting bactericidal antibodies specific to group A streptococcal polysaccharide according to claim 1, wherein the protein component is a native or a recombinant bacterial protein.

7. The method of eliciting bactericidal antibodies specific to group A streptococcal polysaccharide according to claim 6, wherein the protein component is tetanus toxoid, cholera toxin, diphtheria toxoid, or $CRM_{197}$.

8. The method of eliciting bactericidal antibodies specific to group A streptococcal polysaccharide according to claim 7, wherein the protein component is tetanus toxoid.

9. The method of eliciting bactericidal antibodies specific to group A streptococcal polysaccharide according to claim 2, wherein the conjugate is administered with a carrier that is saline, Ringer's solution or phosphate buffered saline.

10. The method of eliciting bactericidal antibodies specific to group A streptococcal polysaccharide according to claim 2, wherein the conjugate is administered with an adjuvant.

11. The method of eliciting bactericidal antibodies specific to group A streptococcal polysaccharide according to claim 10, wherein the adjuvant is aluminum hydroxide, aluminum phosphate, monophosphoryl lipid A, QS21 or stearyl tyrosine.

12. The method of eliciting bactericidal antibodies specific to group A streptococcal polysaccharide according to claim 2, wherein the human is a child.

13. The method of eliciting bactericidal antibodies specific to group A streptococcal polysaccharide according to claim 2, wherein the dosage amount of the administered conjugate is about 0.1 µg to about 10 µg per kilogram of body weight of said mammal.

14. The method of eliciting bactericidal antibodies specific to group A streptococcal polysaccharide according to claim 6, wherein the bacterial protein is a toxin or a toxoid of pseudomonas, staphylococcus, streptococcus, pertussis, or enterotoxigenic *Escherichia coli*.

15. The method of eliciting bactericidal antibodies specific to group A streptococcal polysaccharide according to claim 1, wherein a plurality of the polysaccharide component is bound to the protein component or the protein fragment component.

16. The method of eliciting bactericidal antibodies specific to group A streptococcal polysaccharide according to claim 1, wherein between about 1 and 12 of the polysaccharide component is bound to the protein component or the protein fragment component.

17. The method of eliciting bactericidal antibodies specific to group A streptococcal polysaccharide according to claim 15, wherein the plurality of polysaccharide component in the conjugate is at least 5.

18. The method of eliciting bactericidal antibodies specific to group A streptococcal polysaccharide according to claim 16, wherein the mammal is a human;

n is 3 to 30; and the dosage amount of the administered conjugate is 0.1 µg to about 10 µg per kilogram of body weight of said mammal.

19. The method of eliciting bactericidal antibodies specific to group A streptococcal polysaccharide according to claim 18, wherein the protein component is a native or a recombinant bacterial protein; and the conjugate is administered with an adjuvant.

20. The method of eliciting bactericidal antibodies specific to group A streptococcal polysaccharide according to claim 19, wherein the bacterial protein is tetanus toxoid, cholera toxin, diphtheria toxoid, or $CRM_{197}$.

* * * * *